United States Patent
Mochida et al.

(10) Patent No.: US 7,355,625 B1
(45) Date of Patent: Apr. 8, 2008

(54) ENDOSCOPIC IMAGING SYSTEM AND ENDOSCOPE SYSTEM

(75) Inventors: Akihiko Mochida, Hino (JP); Katsuyuki Saito, Sagamihara (JP); Hideki Tashiro, Machida (JP); Kotaro Ogasawara, Tokyo (JP); Makoto Tsunakawa, Toda (JP); Noboru Kusamura, Hino (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 09/523,332

(22) Filed: Mar. 10, 2000

(30) Foreign Application Priority Data

Mar. 17, 1999 (JP) ............................... H11-072329
Aug. 31, 1999 (JP) ............................... H11-246112

(51) Int. Cl.
  *H04N 7/18* (2006.01)
(52) U.S. Cl. .......................................... 348/65; 348/61
(58) Field of Classification Search .................. 348/61, 348/65, 68, 72, 77; 600/109; 330/149
  See application file for complete search history.

(56) References Cited

U.S. PATENT DOCUMENTS

| | | | | |
|---|---|---|---|---|
| 4,710,807 A | * | 12/1987 | Chikama ..................... | 348/68 |
| 4,992,754 A | * | 2/1991 | Blauvelt et al. ............ | 330/149 |
| 5,178,130 A | * | 1/1993 | Kaiya ......................... | 600/109 |
| 5,196,928 A | * | 3/1993 | Karasawa et al. ............ | 348/65 |
| 5,305,098 A | * | 4/1994 | Matsunaka et al. ........... | 348/65 |
| 5,315,383 A | * | 5/1994 | Yabe et al. .................. | 348/68 |
| 5,398,056 A | * | 3/1995 | Yabe et al. .................. | 348/68 |
| 5,434,615 A | * | 7/1995 | Matumoto .................... | 348/72 |

FOREIGN PATENT DOCUMENTS

| | | |
|---|---|---|
| JP | 63001263 | 1/1988 |
| JP | 05176882 | 7/1993 |
| JP | 06086138 | 3/1994 |
| JP | 06105807 | 4/1994 |

\* cited by examiner

*Primary Examiner*—Allen Wong
(74) *Attorney, Agent, or Firm*—Ostrolenk, Faber, Gerb & Soffen, LLP

(57) ABSTRACT

An imaging apparatus having an imaging device for imaging an object in cooperation with an endoscope is connected to a video processing unit for producing a standard video signal so that it can be disconnected freely. A signal delay occurs over a signal line linking the imaging device and the video processing unit. For this reason, a timing generator and a phase adjustment circuit are incorporated in the imaging apparatus. The timing generator generates driving signals used to drive the imaging device, and the phase adjustment circuit adjusts the phases of the driving signals so that an output signal of the imaging device will be input to the video processing unit according to predetermined timing. Even when the signal line has a different length from any other or the imaging device offers a different number of pixels from any other, the difference can be readily coped with owing to the imaging apparatus. This leads to alleviation of a load incurred by the video processing unit.

21 Claims, 12 Drawing Sheets

FIG.5A CCD OUTPUT SIGNAL
FIG.5B SHa
FIG.5C SHb
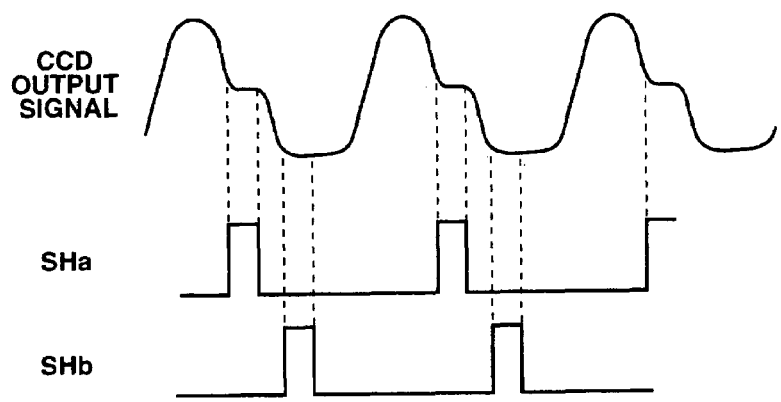
FIG.5D CCD OUTPUT SIGNAL (UNADJUSTED)
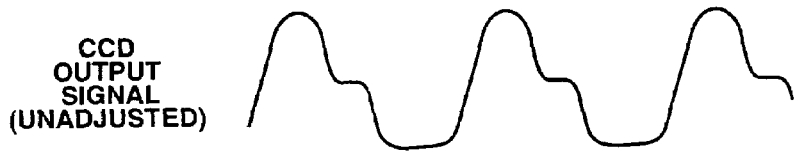
FIG.6
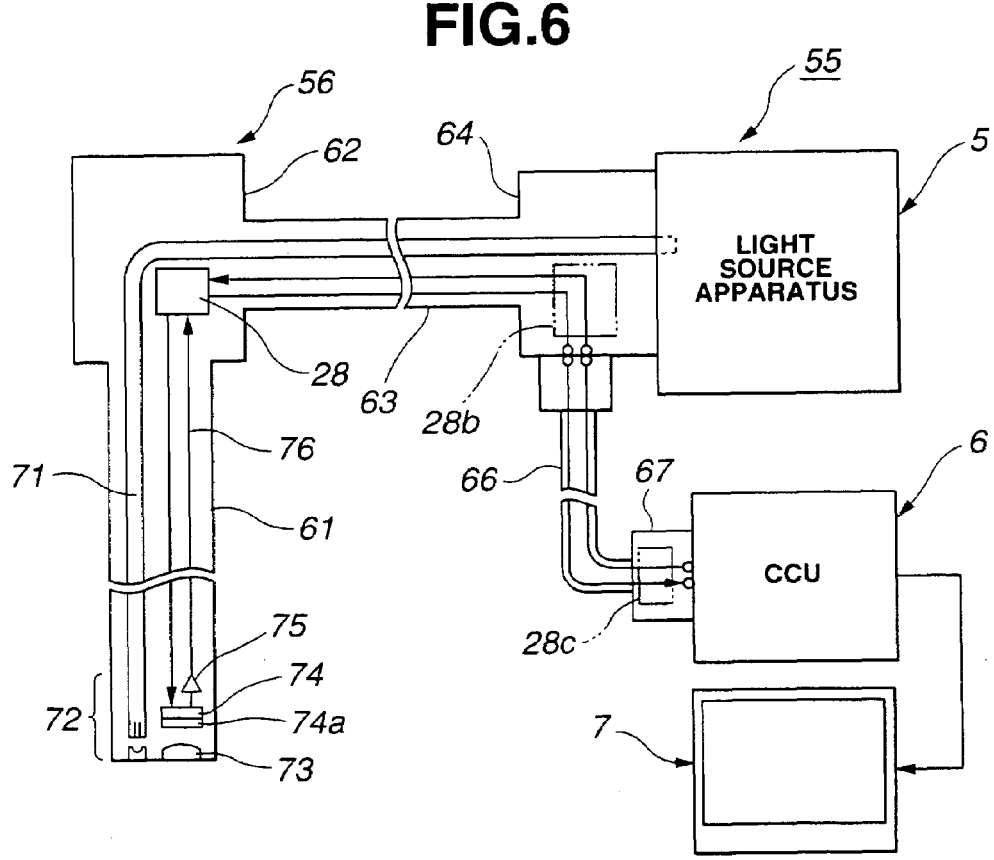

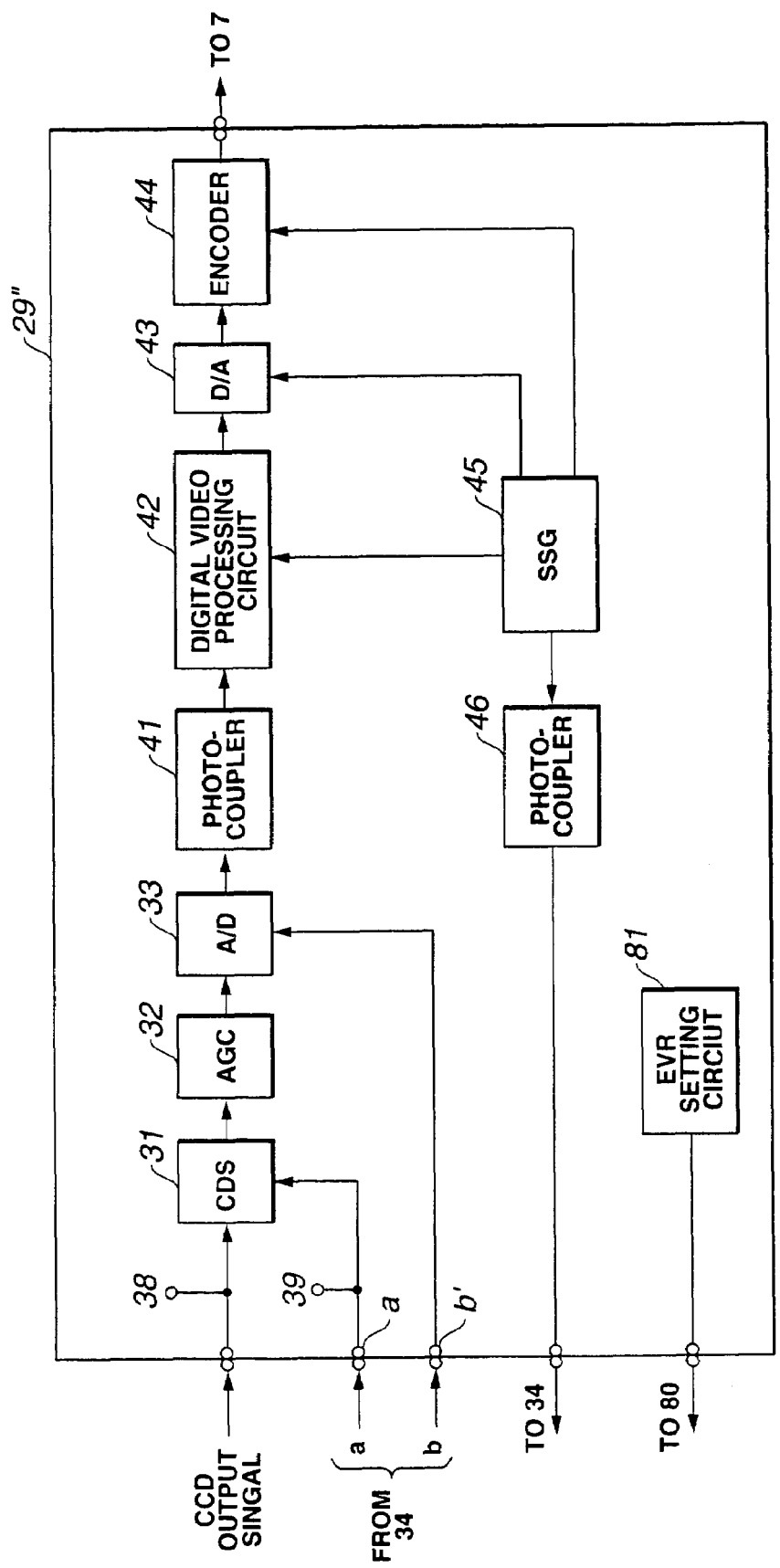

ENDOSCOPIC IMAGING SYSTEM AND ENDOSCOPE SYSTEM

BACKGROUND OF THE INVENTION

1. Field of the Invention

The present invention relates to an endoscopic imaging system and an endoscope system for producing endoscopic images.

2. Description of the Related Art

In recent years, endoscopes have been widely adopted in the fields of medicine and industries. Recently, an endoscopic imaging system having an endoscopic imaging apparatus for producing endoscopic images has come to be used widely. For example, Japanese Unexamined Patent Publication No. 6-86138 has disclosed a related art.

According to the related art, since a signal delay occurs over a cable linking an imaging device and an image processing unit (or video processing unit), a correction needs to be made for cables having different lengths. For this purpose, a reference signal is produced using an output signal of a charge coupled device (CCD). A phase-locked loop (PLL) composed of a phase adjustment circuit, a low-pass filter (LPF), and a voltage-controlled oscillator (VCO) is used to adjust the phases of signals and produce various timing pulses.

A problem with the Japanese Unexamined Patent Publication No. 6-86138 lies in that the PLL is used to adjust the phases of signals and produce various timing pulses in effort to make corrections for cables of different lengths. This makes the circuitry in the image processing unit (or video processing unit) complex. When a plurality of types of electronic endoscopes having cables of different lengths are connected, it is difficult to operate the PLL precisely.

Moreover, a CCD drive circuit is incorporated in the image processing unit (or video processing unit). When solid-state imaging devices that are driven under different conditions are used, drive circuits associated with the solid-state imaging devices must be incorporated in the image processing unit. This results in complex circuitry.

According to related arts disclosed in Japanese Unexamined Patent Publication Nos. 6-105807 and 5-176883, the phases of sampling signals used to perform correlative double sampling are adjusted according to the length of a cable. According to the disclosed methods, the phase of a clock used in a video processing unit for processing a video signal must be adjusted accordingly. Phase difference information stemming from the phase adjustment must be supplied to the video processing unit in any form.

Moreover, the timing of video signal processing must be varied depending on the phase difference information.

Japanese Unexamined Patent Publication No. 63-1263 has disclosed an endoscopic imaging system in which a delay circuit for delaying driving signals used to drive a solid-state imaging device is located around an operation unit of an electronic endoscope.

SUMMARY OF THE INVENTION

An object of the present invention is to provide an endoscopic imaging system and an endoscope system capable of adjusting phases precisely despite its simple configuration. Even when an endoscopic imaging apparatus such as an electronic endoscope having a cable (signal transmission line), whose length is different from other cables, extended therefrom is included in the system, a PLL need not be constructed.

Another object of the present invention is to provide an endoscopic imaging system and an endoscope system making it unnecessary to incorporate a plurality of drive circuits in a video processing unit even when a plurality of solid-state imaging devices that are driven under mutually different conditions is used interchangeably. In short, there is provided an endoscopic imaging system and an endoscope system having a video processing unit used in common among a plurality of solid-state imaging devices that are driven under different conditions because the solid-state imaging devices offer different numbers of pixels and that are used interchangeably.

An endoscopic imaging system comprises:

an endoscope having an illumination optical system for illuminating an object and an objective optical system for introducing an optical image of the object incorporated in an elongated insertion unit thereof;

an imaging apparatus having an imaging device for picking up the optical image;

a video processing unit to which the imaging apparatus is connected so that it can be disconnected freely, and which processes a signal to produce a standard video signal;

a display means for displaying images of the object according to an input standard video signal;

a timing signal generation circuit, incorporated in the imaging apparatus, for generating timing signals used to drive the imaging device; and a phase adjustment circuit for adjusting the phases of the timing signals so as to compensate a signal delay occurring over a signal transmission line to which the imaging device is linked and over which a signal is transmitted.

Even when the signal transmission line has different lengths, the phase adjustment circuit incorporated in the imaging apparatus linked to the signal transmission line precisely adjusts the phases of the driving signals output from the timing signal generation circuit. The imaging device is therefore driven according to the timing of signal processing performed by the video processing unit. This leads to the simplified configuration of the video processing unit.

An endoscope system comprises:

first and second endoscopes each having an illumination optical system for illuminating an object and an objective optical system for introducing an optical image of the illuminated object incorporated in an insertion unit thereof;

first and second imaging apparatuses having first and second imaging devices respectively for picking up optical images produced by the first and second endoscopes respectively;

a video processing unit to which the first and second imaging apparatuses are connected so that they can be disconnected freely and which processes a signal to produce a standard video signal;

a display means for displaying images of the object according to an input standard video signal;

first and second timing signal generation circuits, incorporated in the first and second imaging apparatuses respectively, for generating timing signals used to drive the imaging devices; and first and second phase adjustment circuits for adjusting the phases of the timing signals so as to compensate a signal delay occurring over first and second signal transmission lines to which the first and second imaging devices are linked and over which a signal is transmitted.

Even when the first and second signal transmission lines have different lengths or when the first and second imaging devices are driven under mutually different conditions because they offer different numbers of pixels, the first and second imaging apparatuses produce timing signals and adjust the phases of the timing signals. The video processing unit should merely be used in common and can have the configuration thereof simplified.

BRIEF DESCRIPTION OF THE DRAWINGS

FIG. 1 to FIG. 7D relate to the first embodiment of the present invention;

FIG. 1 is a block diagram showing the configuration of an endoscopic imaging system in accordance with the first embodiment;

FIG. 2 is a block diagram showing the electric configurations of a TV camera serving as an endoscopic imaging apparatus and a pre-processing circuit;

FIG. 3 is a block diagram showing the electric configuration of a CCU;

FIG. 4 is a circuit diagram showing the configuration of a phase adjustment circuit;

FIGS. 5A to 5D are explanatory diagrams indicating the signal wave sampling action of a correlative double sampling (CDS) circuit;

FIG. 6 is a block diagram showing the configuration of an endoscopic imaging system in which an electronic endoscope is employed;

FIG. 7B and FIG. 7D are timing charts concerning CCD driving signals;

FIG. 8 is a block diagram showing the configuration of a TV camera employed in the second embodiment;

FIG. 9 is a block diagram showing the electric configuration of a video processing circuit in a CCU;

FIG. 10 is a circuit diagram showing the configuration of a phase adjustment circuit;

FIG. 11 is a circuit diagram showing the configuration of a phase adjustment circuit employed in the first variant;

FIG. 12 is a circuit diagram showing the configuration of a phase adjustment circuit employed in the second variant;

FIG. 13 shows a characteristic line indicating a characteristic of a delay device;

FIG. 14 is a block diagram showing the configuration of an endoscopic imaging system in accordance with the third embodiment;

FIG. 15 is a block diagram showing the electric configurations of a TV camera serving as an endoscopic imaging apparatus and a processing circuit;

FIG. 16 is a block diagram showing the electric configuration of a video processing circuit in a CCU;

FIG. 17 is a block diagram showing the configuration of an endoscopic imaging system in which an electronic endoscope is employed;

FIG. 18 is a block diagram showing an example of the configuration of an endoscope system;

FIG. 19 and FIG. 20 relate to the fourth embodiment of the present invention;

FIG. 19 is a block diagram showing the electric configurations of a TV camera and a processing circuit employed in the fourth embodiment; and FIG. 20 is a block diagram showing the electric configuration of a video processing circuit in a CCU.

DESCRIPTION OF PREFERRED EMBODIMENTS

Figure 1:
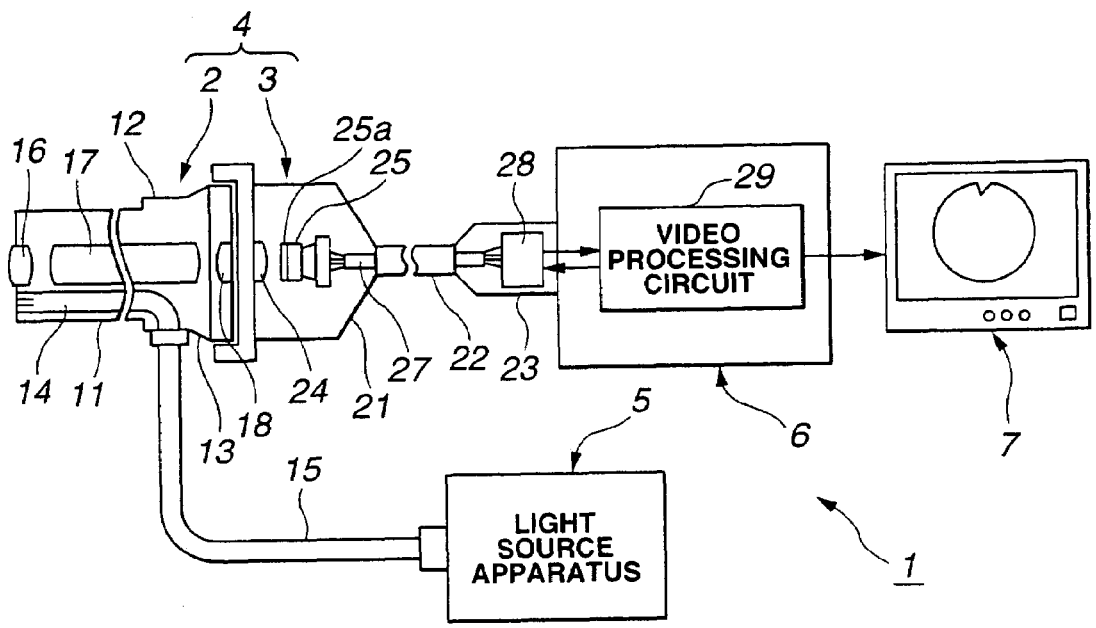

Referring to the drawings, embodiments of the present invention will be specifically described below.

First Embodiment

The first embodiment of the present invention will be described with reference to FIG. 1 to FIG. 7D.

As shown in FIG. 1, an endoscopic imaging system 1 in accordance with the first embodiment of the present invention consists mainly of an endoscope 4 with an external TV camera, a light source apparatus 5, a camera control unit (hereinafter abbreviated to CCU) 6, and a TV monitor 7. The TV-camera mounted endoscope 4 has TV camera 3 (serving as an endoscopic imaging apparatus), which includes an imaging means, mounted on an optical endoscope 2. The light source apparatus 5 supplies illumination light to the optical endoscope 2. The CCU 6 is removably connected to the TV camera 3 so that it can be disconnected freely. The CCU 6 processes a video signal to produce a standard video signal. The TV monitor 7 displays endoscopic images according to the video signal output from the CCU 6.

The optical endoscope 2 is a rigid endoscope having, for example, a rigid insertion unit 11, a hand-held unit (operation unit) 12 formed at the rear end of the insertion unit 11, and an eyepiece unit 13 formed at the rear end of the hand-held unit 12.

A light guide 14 is passed through the insertion unit 11, and connected to the light source apparatus 5 by way of a light guide cable 15 linked to a light guide base of the hand-held unit 12. White illumination light emanating from a lamp, which is not shown, in the light source apparatus 5 is propagated and emitted from the distal surface of the light guide 14. An object such as a lesion is thus illuminated.

An objective lens 16 is included in the distal part of the insertion unit 11. An optical image introduced by the objective lens 16 is propagated backward along, for example, a system of relay lenses 17. Thus, the object can be visualized while magnified through an eyepiece lens 18 included in the eyepiece unit 13.

Moreover, the TV camera 3 consists of a camera head 21, a camera cable 22, and a connector 23. The camera head 21 is mounted on (the external surface of) the eyepiece unit 13 so that it can be dismounted freely. The camera cable 22 (serving as a signal transmission line) is extended from the camera head 21. The connector 23 is attached to the proximal end of the camera cable 22, and removably coupled to the CCU 6 so that it can be uncoupled freely.

An image formation lens 24 is incorporated in the camera head 21 so that it will be opposed to the eyepiece lens 18. A charge coupled device (abbreviated to CCD) 25 serving as a solid-state imaging device is located at the position of the image plane of the image formation lens 24. A mosaic filter 25a is placed on the face of the CCD 25 for photoelectrically converting an optical image. The mosaic filter 25a optically divides an object image into color images and routes them into the imaging surface of the CCD 25.

A printed-circuit board forming a buffer amplifier 26 (see FIG. 2) is placed on the back of the CCD 25. One end of the camera cable 22 (or a signal cable 27 contained in the camera cable 22) is linked to the CCD 25 and printed-circuit board. The other end thereof is linked to an electrical contact of the connector 23 via a pre-processing circuit 28 included in the connector 23.

A CCD output signal output from the CCD 25 has its component sampled by a correlative double sampling (CDS) circuit 31 to be described later. At this time, the CCD output signal is delayed while passing through the signal cable 27 and therefore lags behind. The pre-processing circuit 28 is therefore provided with a circuit element for adjusting in advance the phases of driving signals used to drive the CCD so that the CDS circuit 31 can sample a component of the CCD output signal correctly.

When the connector 23 is coupled to the CCU 6, the pre-processing circuit 28 is electrically connected to a video processing circuit 29 incorporated in the CCU 6. The video processing circuit 29 outputs a produced standard video signal to the TV monitor 7.

Figure 2:
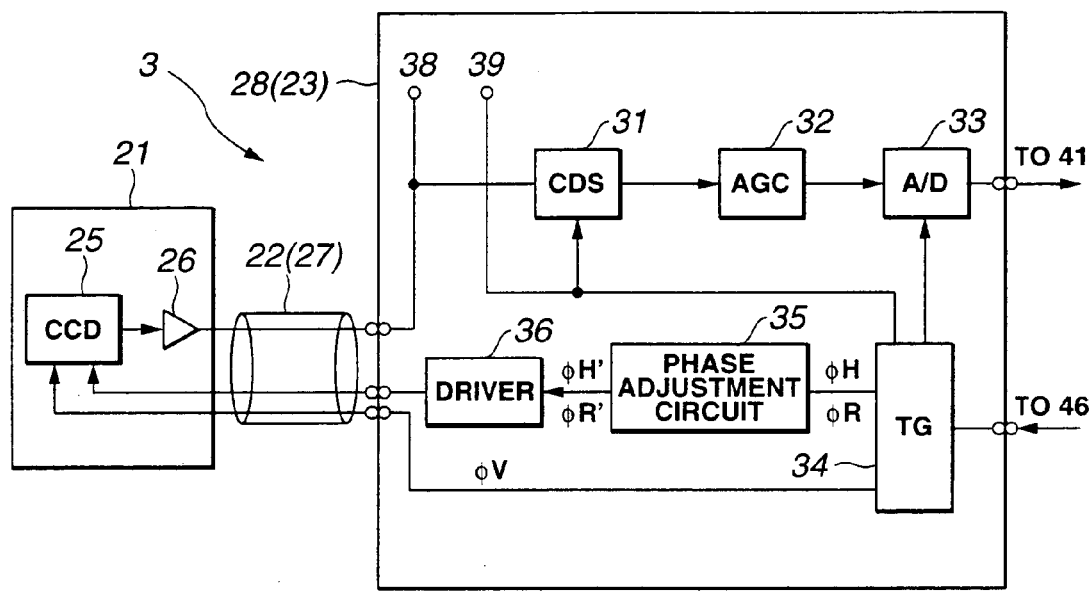

As shown in FIG. 2, the CCD 25 and buffer amplifier 26 are incorporated in the camera head 21.

The correlative double sampling (CDS) circuit 31, an automatic gain control (AGC) circuit 32, and an A/D conversion circuit 33 are included in the pre-processing circuit 28 in the connector 23. The CDS circuit 31 samples a component of the CCD output signal according to a correlative double sampling method. The AGC circuit 32 adjusts the output signal of the CDS circuit 31 up to a proper level. The A/D conversion circuit 33 converts an AGC output signal into a digital form.

The pre-processing circuit 28 has a timing generator (TG) 34 for generating timing signals. The timing generator 34 supplies the timing signals to the CDS circuit 31 and A/D conversion circuit 33, and also generates CCD driving signals.

The CCD driving signals, for example, a horizontal driving signal φH used for horizontally drive the CCD and a reset signal φR used to reset the CCD are applied to the CCD 25 by way of a phase adjustment circuit 35 and a cable driver 36. A vertical driving signal φV used to vertically drive the CCD and serving as another CCD driving signal is applied directly to the CCD 25 while bypassing the phase adjustment circuit 35 and cable driver 36.

Figure 3:
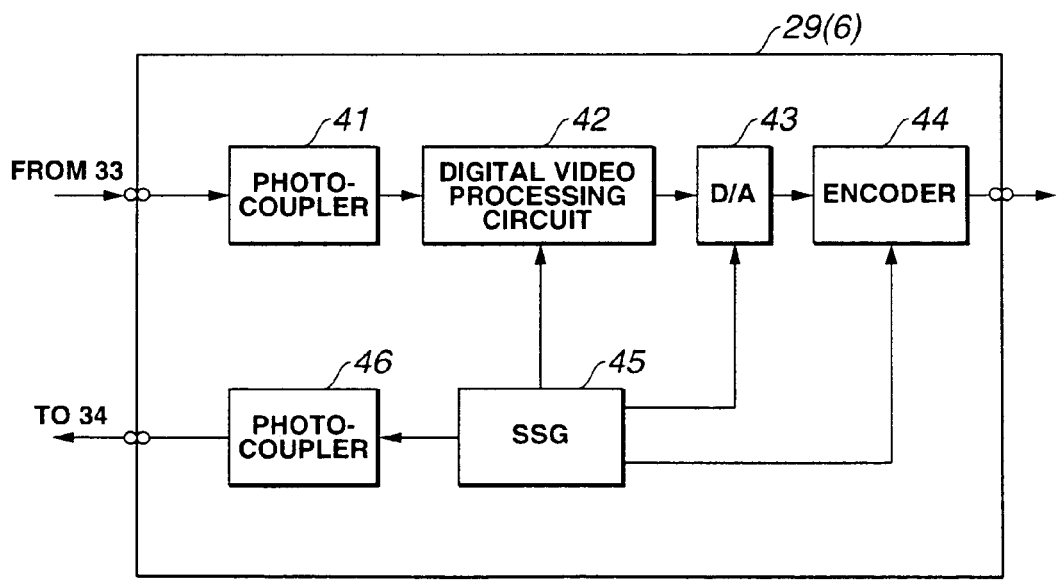

As shown in FIG. 3, in the video processing circuit 29 incorporated in the CCU 6, a digital video processing circuit 42 (formed with, for example, a DSP) processes a digital video signal output from the pre-processing circuit 28 via a photocoupler 41. A D/A conversion circuit 43 converts the digital signal into an analog signal, and an encoder 44 converts the signal into a standard video signal such as an NTSC-conformable signal. The encoder 44 then outputs the NTSC signal to the TV monitor 7.

A sync signal generator (SSG) 45 supplies various sync signals to the digital video processing circuit 42, D/A conversion circuit 43, and encoder 44. The sync signal generator 45 also supplies a sync signal to the timing generator 34 included in the pre-processing circuit 28 via a photocoupler 46.

The photocouplers 41 and 46 serve as isolation means for electrically isolating a patient circuit from a secondary circuit.

According to the present embodiment, a digital video signal having a predetermined phase and having a certain phase relationship to a sync signal is supplied from the TV camera 3 to the video processing circuit 29 in the CCU 6. The camera cable 22, which can have any desired length is adopted for the TV camera 3 (the difference in the length of the cable is corrected by the TV camera 3). Nevertheless, a common digital video signal is input to the video processing circuit 29 in the CCU 6. The common digital video signal is processed in order to produce a standard video signal. The standard video signal is then output to the TV monitor 7.

Owing to the foregoing constituent features, the circuitry of the CCU 6 can be simplified. When the CCD 25 is driven under different conditions from any other because it offers a different number of pixels from any other, the driving conditions can be set precisely owing to the timing generator 34 incorporated in the TV camera 3. The circuitry in the CCU 6 can be used in common.

Figure 4:
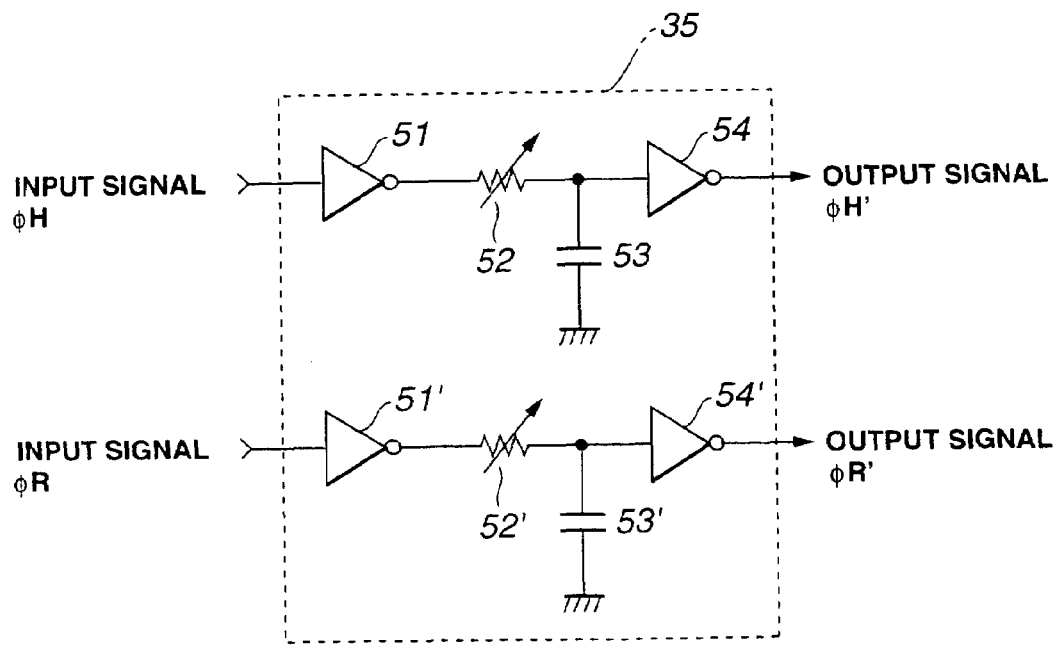

FIG. 4 shows the configuration of the phase adjustment circuit 35. As shown in FIG. 4, the phase adjustment circuit 35 adjusts the phases of the horizontal driving signal φH and reset signal φR that are input signals using the same systems of circuit elements.

The horizontal driving signal φH and reset signal φR output from the timing generator 34 are input to inverters 51 and 51' shown in FIG. 4. Consequently, a horizontal driving signal φH' and a reset signal φRφ resulting from phase adjustment are output from inverters 54 and 54' via phase change circuits composed of variable resistors 52 and 52' and capacitors 53 and 53' respectively.

The phase adjustment circuit having the simple configuration is used to precisely adjust the phases of the input signals. Consequently, the relationship between the CCD signal and sampling pulses SHa and SHb used by the CDS circuit 31 becomes as shown in FIG. 5A, FIG. 5B, and FIG. 5C.

The CDS circuit 31 outputs the sampling pulse SHa to sample the level of a feedthrough of the CCD output signal. The sampling pulse SHb is output in order to sample the level of a signal wave.

FIG. 5D shows the CCD output signal whose phase has not been adjusted. In this case, the CCD output signal actually input to the CDS circuit 31 in the pre-processing circuit 28 located near the video processing circuit 29 lags behind an undelayed signal because the CCD output signal is delayed while passing through the signal cable 27. Incidentally, the pre-processing circuit 28 processes a signal synchronously with a sync signal output from the video processing circuit 29. Therefore, even if the CDS circuit attempted to sample the feedthrough and signal wave of the CCD output signal using the sampling pulses SHa and SHb, the CDS circuit would fail.

The phase adjustment circuit 35 retards the timing of outputting the CCD driving signals. Phase adjustment is thus achieved so that the feedthrough and signal wave of the CCD output signal expressing the next pixel, which are shown in FIG. 5A, will be in phase with the sampling pulses SHa and SHb shown in FIG. 5B and FIG. 5C.

For the phase adjustment, the variable resistors 52 and 52' shown in FIG. 4 are used. The variable resistors are regulated while the waveforms of signals detected at test pins 38 and 39 shown in FIG. 2 are observed using an oscilloscope or the like. The phase adjustment can thus be achieved precisely.

The horizontal driving signal φH' and reset signal φR' resulting from phase adjustment are amplified up to a level permitting flow of current required for driving performed by the driver 36, and supplied to the CCD 25.

According to the present embodiment, the phase adjustment circuit 35 is included for phase adjustment. The CDS circuit 31 is included for accurately sampling a signal wave.

To be more specific, the CDS circuit 31 to which an output signal of the CCD 25 serving as an imaging device is input samples a signal wave. If the CDS circuit sampled the signal wave using a sampling pulse, it would fail to sample the signal wave correctly. This is because of a signal delay occurring over the camera cable 22 (signal cable 27). According to the present embodiment, the variable resistors 52 and 52' included in the phase adjustment circuit 35 are used to adjust the phases of the CCD driving signals in advance. Thus, the phase of the output signal of the CCD 25 is agreed with the timing of the CDS circuit 31's sampling a signal wave.

In this case, the phase adjustment circuit 35 is included in the imaging apparatus, or more particularly, in the TV camera 3. In other words, the TV camera 3 adjusts phases. Therefore, even when the TV camera 3 having the camera cable 22 (or signal cable 27), whose length may vary, extended therefrom is connected to the CCU 6, the TV camera 3 can cope with the difference in the length between different cables. The circuitry in the CCU 6 need not be made complex.

According to the present embodiment, a phase shift of a signal occurring through a transmission path is corrected immediately before the signal is input to the CCU 6. The CCU 6 can therefore process the video signal according to predetermined timing while being unaffected by the phase shift.

The phase adjustment circuit 35 adjusts the phases of the CCD driving signals in consideration of the adverse effect of a signal delay occurring over the signal cable 27, so that a signal delay occurring over the signal cable 27 can be canceled. Consequently, a signal wave is input to the CDS circuit 31 according to predetermined timing (irrespective of the length of the signal cable 27). The CDS circuit 31 converts the signal wave into a baseband video signal.

Operations to be exerted by the present embodiment will be described below.

Illumination light emanating from a lamp in the light source apparatus 5 is propagated over the light guide 14 in the optical endoscope 2 after passed through the light guide cable 15. The illumination light is then emitted forward from the distal surface of the light guide 14 in the distal part of the insertion unit 11. An object such as an intracavitary region of a patient is thus illuminated.

Reflected light returning from the illuminated object is introduced by the objective lens 16 located in the distal part of the insertion unit, and passed through the system of relay lenses 17, which serves as an image propagating means, incorporated in the endoscope 2. Consequently, the CCD 25 picks up the light. The image propagating means may be realized with, aside from the system of relay lenses, an image guide fiber bundle.

With application of the CCD driving signals, the CCD 25 photoelectrically converts the light and accumulates electrical charges. The buffer amplifier 26 amplifies the current of the charges to be transmitted over the cable, and outputs the resultant current as a CCD output signal to the connector 23 by way of the camera cable 22. The CCD output signal is sampled by the CDS circuit 31 according to the correlative double sampling method.

Sampling signals are supplied from the timing generator 34. The phase adjustment circuit 35 adjusts phases so that the CCD output signal and the sampling pulses will establish the relationship shown in FIG. 5A to FIG. 5C.

The CCD output signal is transmitted over the camera cable 22. A signal delay occurs. Unless the delay is compensated, the relationship shown in FIG. 5A to FIG. 5C will be broken (see FIG. 5D).

For compensating the delay, the phases of the CCD driving signals are adjusted.

Specifically, as shown in FIG. 4, the horizontal driving signal φH and reset signal φR (output from the timing generator 34) are input to the phase adjustment circuit 35. The variable resistors 52 and 52' are regulated in order to adjust the phases of the horizontal driving signal φH and reset signal φR so that the CCD output signal and the sampling pulses SHa and SHb will establish the relationship shown in FIG. 5A to FIG. 5C.

In other words, the phases of the horizontal driving signal φH and reset signal φR are adjusted so that the sampling pulse SHa will be in phase with a feedthrough of the CCD output signal and the sampling pulse SHb will be in phase with an signal wave thereof. For regulating the variable resistors 52 and 52' so as to adjust the phases, the waveforms of signals detected at the test pins 38 and 39 are observed using an oscilloscope or the like.

The phase adjustment circuit 35 shown in FIG. 4 delays the phases of input signals to thus cause the input signals to lag behind. When, for example, the signal cable 27 is long, the magnitude of delay is made small. When the signal cable 27 is short, the magnitude of delay is made large. Irrespective of the length of the signal cable 27, the phases of the input signals should merely be delayed and thus adjusted.

The horizontal driving signal φH and reset signal φR whose phases have been adjusted are amplified up to a level permitting flow of current required for driving performed by the driver 36, and then supplied to the CCD 25.

The cycle of the vertical driving signal φV is longer than that of the horizontal driving signal φH (for reference, the frequency of the signal φV is 15.734 kHz, and that of the signal φH is 14.31818 MHz). An adverse effect of a delay of the vertical driving signal φV proportional to the length of the cable can therefore be ignored.

However, when the cable length is very large (normally, the cable length is about 4 m) (when the cable length exceeds, for example, 10 m), the adverse effect of the delay cannot be ignored. In this case, the phase of the vertical driving signal φV may also be adjusted.

After phase adjustment is carried out as mentioned above, the CDS circuit 31 samples the level of the feedthrough of the CCD output signal and that of the signal wave thereof, and extracts a difference component between them. The signal wave is then input to the AGC circuit 32. After amplified, the resultant signal is digitized by the A/D conversion circuit 33 and input to the video processing circuit 29 in the CCU 6. The digital signal is then converted into a standard video signal by the video processing circuit 29, and input to the TV monitor 7. Consequently, endoscopic images are displayed.

A clock, a horizontal sync signal, and a vertical sync signal are supplied from the sync signal generator 45 in the CCU 6 to the timing generator 34 via the photocoupler 46.

The present embodiment has advantages described below.

In the past, differences in cable length have been compensated for by using a PLL or the like. According to the present embodiment, differences in cable length of a cable are compensated within the TV camera 3 serving as an endoscopic imaging apparatus. The compensation can be achieved with the simple configuration described herein.

According to the related arts, the circuitry in the video processing unit cannot help becoming complex in order to correct for differences in the length of cables. When a solid-state imaging device that must be driven under different conditions from any other is employed, an associated drive circuit is needed. According to the present embodiment, the endoscopic imaging apparatus can cope with differences in cable length of a cable. The necessity of an associated drive circuit is obviated, and the configuration of the CCU 6 serving as a video processing unit can be simplified.

According to the present embodiment, the phases of driving signals are adjusted according to the length of a cable. When sampling signals used for correlative double sampling become in phase with a clock produced in the CCU 6, sampling is carried out. It becomes therefore unnecessary for the CCU 6 to grasp a phase difference (occurring but for the constituent features of the present embodiment) and correct it during signal processing. From this viewpoint, signal processing performed by the CCU 6 and signal processing performed by the TV camera 3 can be separated from each other.

Moreover, the present embodiment can be implemented in an endoscopic imaging system adopting an electronic endoscope (or a video-scope) (serving as an endoscopic imaging apparatus) that has, as shown in FIG. 6, a solid-state imaging device incorporated in the distal part thereof.

An endoscopic imaging system 55 shown in FIG. 6 consists mainly of an electronic endoscope 56, the light source apparatus 5, the CCU 6, and the TV monitor 7. The electronic endoscope 56 has a built-in imaging means. The light source apparatus 5 supplies illumination light to the electronic endoscope 56. The CCU 6 processes a signal to produce a video signal. The TV monitor 7 displays endoscopic images according to the video signal output from the CCU 6.

The electronic endoscope 56 consists mainly of an insertion unit 61, an operation unit 62, a universal cable 63, and a connector unit 64. The insertion unit 61 is inserted into a body cavity. The operation unit 62 is an endoscope portion to be held by an operator and has switches, which are not shown, formed thereon. The universal cable 63 is extended from the operation unit 62. The connector unit 64 is attached to the proximal end of the universal cable 63. A light guide base projecting from the front end of the connector unit 64 is removably coupled to the light source apparatus 5 so that it can be uncoupled freely.

One end of a cable 66 is linked to the connector unit 64. A connector 67 attached to the other end of the cable 66 is removably coupled to the CCU 6 so that it can be uncoupled freely.

A light guide fiber bundle 71 over which illumination light travels is passed through the insertion unit 61. A light guide base attached to the rear end of the light guide fiber bundle 71 is coupled to the light source apparatus 5, whereby illumination light emanating from the light source apparatus 5 is supplied. The supplied illumination light is propagated and emitted from the distal surface of the light guide fiber bundle 71 located in a distal part 72 of the insertion unit 61 to an object such as a lesion through an illumination lens. The object is thus illuminated.

An objective lens 73 is locked in the distal part 72, and a CCD 74 is located at the position of the image plane of the objective lens 73. A mosaic filter 74a is placed on the imaging surface of the CCD 74, and optically separates an object image into color images. A buffer amplifier 75 is located at a signal output terminal of the CCD 74.

The CCD 74 (and buffer amplifier 75) is connected to the CCU 6 over a signal line 76 passing through the insertion unit 61, operation unit 62, and universal cable 63 respectively and over a signal line contained in the cable 66. In the endoscopic imaging system 55, the pre-processing circuit 28 (shown in FIG. 2) is incorporated in, for example, the electronic endoscope 56.

In the case of the electronic endoscope 56, the operation unit 62 has a space large enough to incorporate the pre-processing circuit 28 therein. Alternatively, as the pre-processing circuit may be located at a position 28b in the connector unit 64 or a position 28c in the connector 67 which is indicated with a double dashed line in FIG. 6.

According to the present embodiment, an endoscope system described below may be constructed using the components shown in FIG. 1 and FIG. 6.

That is, the endoscope system may comprise an endoscope 4 with an external TV camera, the electronic endoscope 56, and the CCU 6. The endoscope 4 with an external TV camera and the electronic endoscope 56 (serving as first and second endoscopic imaging apparatuses) have the CCDs 25 and 74 respectively as solid-state imaging devices and have cables of different lengths extended therefrom. The endoscope 4 with an external TV camera and the electronic endoscope 56 are selectively connected to the CCU 6 so that they can be disconnected freely. The CCU 6 processes common video signals of the two types of endoscopes.

The endoscope system has the pre-processing circuit 28 incorporated in the endoscope 4 with an external TV camera and the electronic endoscope 56 respectively. The pre-processing circuit 28 comprises of the timing generator 34 for generating CCD driving signals and sampling signals used to sample an signal wave of a CCD output signal, and the phase adjustment circuit 35 for adjusting the phases of the CCD driving signals. The endoscope 4 with an external TV camera and the electronic endoscope 56 each adjust the phases of the driving signals according to the length of the cable extending therefrom. A predetermined digital video signal that has been adjusted to be in phase with the sampling pulses used by the CDS circuit 31 can be input to the common CCU 6. The common CCU 6 then produces a standard video signal. Consequently, endoscopic images are displayed on the TV monitor 7. Incidentally, the phases of the sampling pulses and a horizontal sync signal establish a predetermined relationship.

Even in the endoscope system, the endoscope 4 with an external TV camera or the electronic endoscope 56 can compensate for differences in cable lengths. Differences in cable lengths can therefore be compensated for precisely. Moreover, the circuitry in the CCU 6 can be simplified.

In the above description, the lengths of the cables extending from the endoscope with an external TV camera and the electronic endoscope are different from each other. Further, the endoscope with an external TV camera and the electronic endoscope may be mutually different in terms of the conditions for driving a CCD. Even in this case, the configuration of the CCU 6 will be simplified.

Assume that the CCD 25 and CCD 74 offer mutually different numbers of pixels. The number of pulses of CCD driving signals output from the timing generator 34 must be varied depending on the number of pixels. Even in this case, a CDS output signal sampled using sampling pulses that are synchronous with a horizontal sync signal while exhibiting a certain phase is input to the CCU 6. The CCU 6 should merely process a signal according to a common procedure all the time. Incidentally, the duration of a picture signal contained in the CCD output signal and expressing endoscopic images is different between the CCD 25 and CCD 74.

Figure 7A:
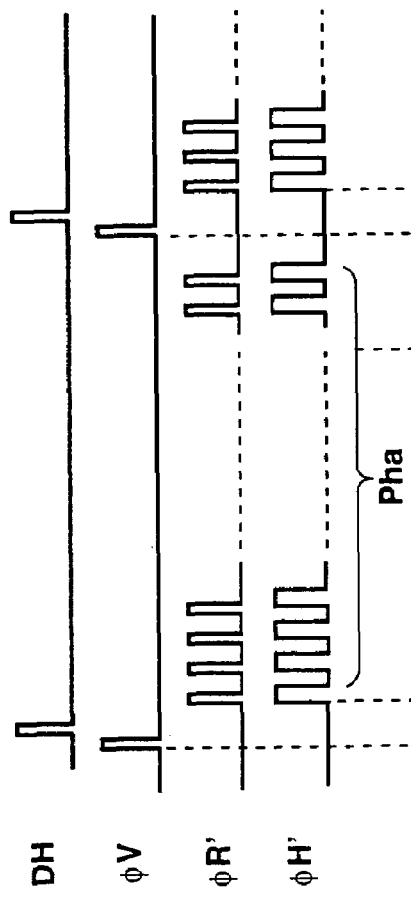
FIG. 7A and FIG. 7C are concerned with two CCDs offering different numbers of pixels.
Figure 7B:
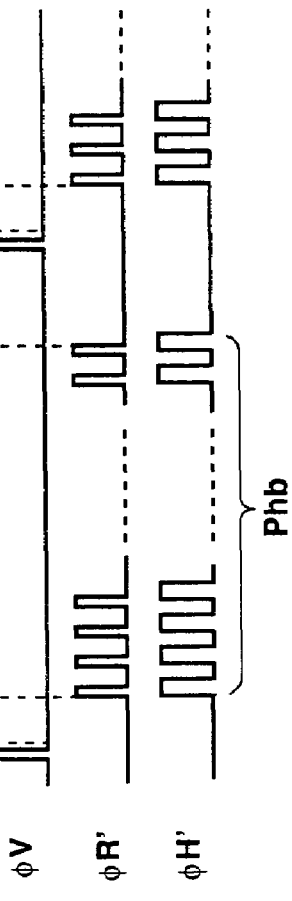
Figure 7C:
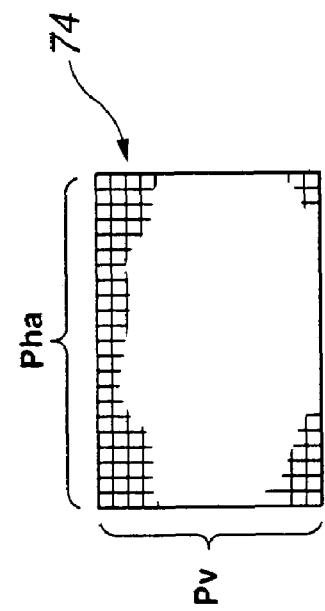

A description will proceed with reference to FIG. 7A to FIG. 7D. FIG. 7A and FIG. 7C show the pixels offered by the CCD 74 and CCD 25 respectively. The number of vertically lined pixels offered by the CCD 74 is Pv, while the number of horizontally lined pixels is Pha. The number of vertically lined pixels offered by the CCD 25 is Pv, while the number of horizontally lined pixels is Phb. Pha is larger than Phb.

Figure 7D:
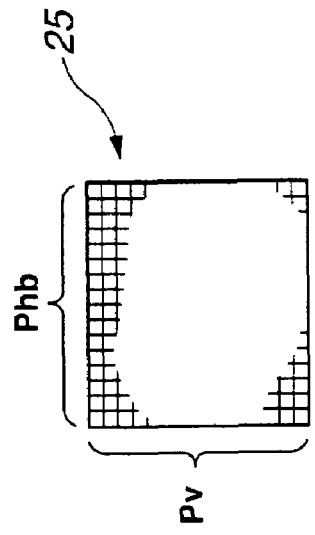

In this case, CCD driving signals ($\phi$V, $\phi$R', $\phi$H') used to drive the CCD 74 have waveforms shown in FIG. 7B, and CCD driving signals (φV, φR', φH') used to drive the CCD 25 have waveforms shown in FIG. 7D.

The timing generator 34 involved in driving the CCD 74 and the timing generator 34 involved in driving the CCD 25 produce signals φV having the same number of pulses. However, the numbers of pulses contained in signals φR and φH are different between the timing generators. These signals are passed through the phase adjustment circuits 35. This results in the CCD driving signals (φV, φR', φH') exhibiting phases shown in FIG. 7B and FIG. 7D.

When one signal φV is output to the CCD 74 offering a larger number of pixels, signals φR' and signals φH' each numbering Pha are output. In contrast, a signal φV is output to the CCD 25 so that the signal will exhibit the same cycle as the above signal φV. When one signal φV is output, signals φR' and φH' numbering Phb are output.

Referring to FIG. 7B and FIG. 7D, the cycle of the signal φV is agreed with that of a horizontal sync signal DH output from the video processing unit 29. The horizontal sync signal DH is synchronous with sampling pulses SHa and SHb shown in FIG. 5B and FIG. 5C while exhibiting a certain phase relative to the sampling pulses owing to a base clock that is not shown. The sampling pulses SHa and SHb are output from the CDS circuit 31 for sampling. The phases of the signals φR' and φH' are adjusted so that the specific waves of a CCD output signal will be in phase with the sampling pulses SHa and SHb.

Referring to FIG. 7B and FIG. 7D, the signals φR' and φH' have the phases thereof adjusted. Even if the signal φV having the phase thereof unadjusted and being destined for the CCD 74 and the signal φV having the phase thereof unadjusted and being destined for the CCD 25 are slightly out of phase, signal processing will remain unaffected. The common CCU 6 will produce a standard video signal.

For brevity's sake, the CCDs offering different numbers of horizontally lined pixels have been described with reference to FIG. 7A to FIG. 7D. The foregoing constituent features can cope with CCDs offering different numbers of vertically lined pixels or offering different numbers of horizontally lined pixels and different numbers of vertically lined pixels alike.

According to the present system, the timing generator 34 is incorporated in both the endoscope 4 with an external TV camera and the electronic endoscope 56. Even when the CCDs included in the endoscopes offer different numbers of pixels, the difference can be coped with owing to the timing generators 34.

In contrast, according to the Japanese Unexamined Patent Publication No. 63-1263, a driving pulse generation circuit is incorporated in a video processing unit (video processor). In this case, when endoscopes offering different numbers of pixels are employed, it is hard to cope with the difference.

Second Embodiment

Next, the second embodiment of the present invention will be described with reference to FIG. 8 to FIG. 13.

The present embodiment is different from the first embodiment in the configuration of the pre-processing circuit 28 shown in FIG. 2. That is to say, an electronic voltage regulator (hereinafter abbreviated to an EVR) 80 is connected to the phase adjustment circuit 35 (see FIG. 8). A control signal is supplied from an EVR setting circuit 81 included in the video processing circuit 29 in the CCU 6 shown in FIG. 9 to the EVR 80.

An input signal of the CDS circuit 31 and sampling pulses output from the timing generator 34 are input to the video processing circuit 29 in the CCU 6. The waveforms of the signals can be observed at test pins 82 and 83 in the video processing circuit 29.

Figure 10:
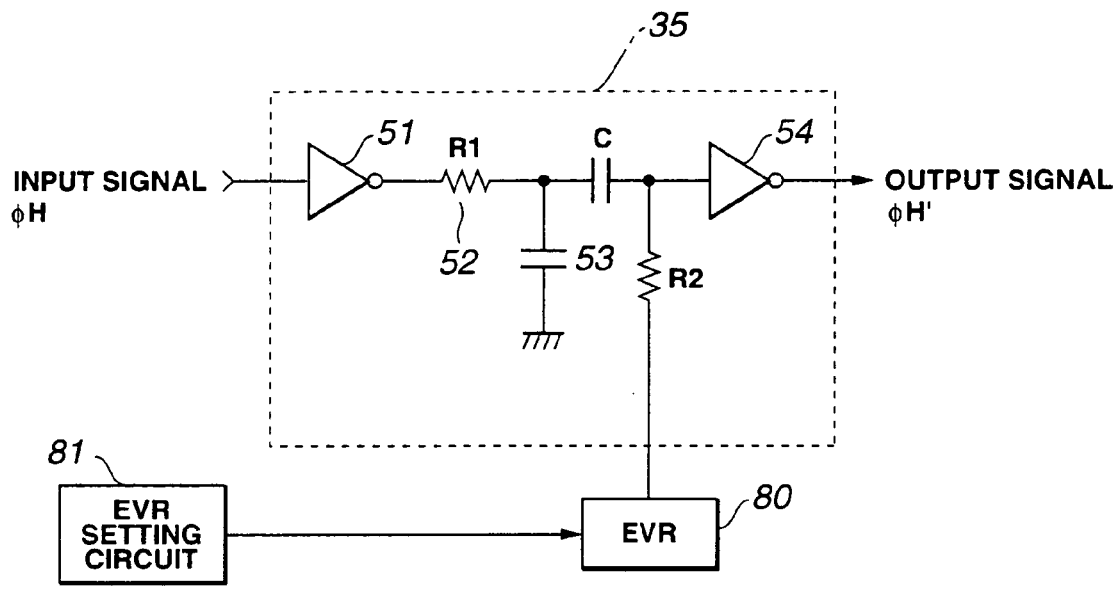

FIG. 10 shows the configuration of the phase adjustment circuit 35 in accordance with the present embodiment. The phase adjustment circuit 35 is different from the phase adjustment circuit 35 shown in FIG. 4 in the points described below. Namely, a resistor R1 whose resistance is set to a fixed value is substituted for the variable resistor 52. A capacitor C is interposed between the resistor R1 and an inverter 54. The EVR 80 is connected to a node between the capacitor C and inverter 54 via a resistor R2.

A voltage output from the EVR 80 is varied depending on a setting signal sent from the EVR setting circuit 81. The inverter 54 provides an output, of which level is opposite to that of an input thereof, with the level thereof set to a threshold level that is a high or low level. Thus, the phase of each driving signal is adjusted. FIG. 10 shows the circuit elements of the phase adjustment circuit that treat a horizontal driving signal φH. The same circuit elements are included for treating a reset signal φR.

Operations to be exerted by the present embodiment will be described below.

The phase adjustment circuit 35 employed in the present embodiment has the circuit elements shown in FIG. 10. The phases of a horizontal driving signal φH and a reset signal φR which are output from the timing generator 34 are adjusted by the phase adjustment circuit 35, whereby a horizontal driving signal φH' and a reset signal φR' are produced. The horizontal driving signal φH' and reset signal φR' are applied together with a vertical driving signal φV to the CCD 25.

Figure 9:
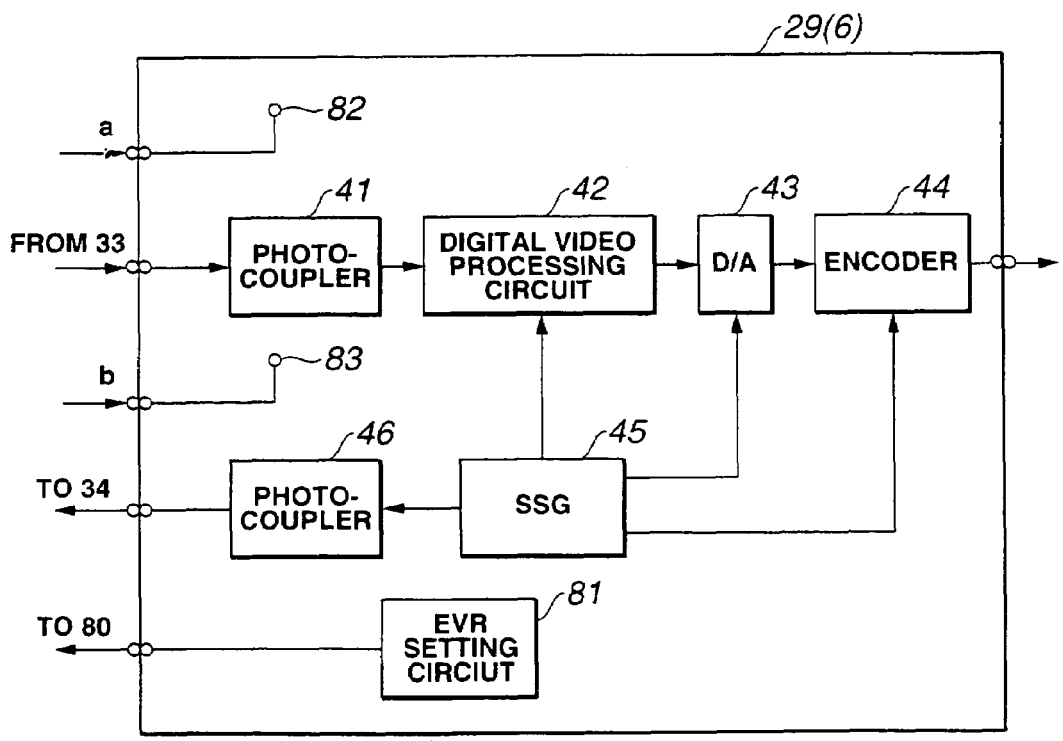

A signal representing data read from the CCD 25 is passed through the CDS circuit 31 in the pre-processing circuit 28 and input to the video processing circuit 29 in the CCU 6 shown in FIG. 9. A control voltage provided by the EVR 80 is applied to the phase adjustment circuit 35. Consequently, the phases of the driving signals are adjusted so that the phases of a CCD output signal and sampling pulses will have the relationship shown in FIG. 5A to FIG. 5C.

The phase adjustment is achieved as described below. Namely, while the waveforms of voltages detected at the test pins 82 and 83 in the CCU 6 are observed, the EVR setting circuit 81 is used to produce a control signal accordingly. With the control signal, a voltage value is set in the EVR 80 in the pre-processing circuit 28 within the connector 23 of the TV camera 3.

The present embodiment has the same advantages as the first embodiment. In addition, the phases of driving signals are adjusted via the EVR 80 using the CCU 6. This obviates the necessity of including a regulating means such as a trimmer or a variable resistor in the connector 23. It is also unnecessary to bore a regulation hole or the like, which is used for regulation, in the connector unit. A design for fully sealing the connector 23 can be adopted, and the TV camera 3 can be readily structured to be waterproof. The efficiency in shielding components from electromagnetic waves can be improved.

Similarly to the first embodiment, the present embodiment can be implemented in an endoscopic imaging system including the electronic endoscope 56 shown in FIG. 6.

Figure 11:
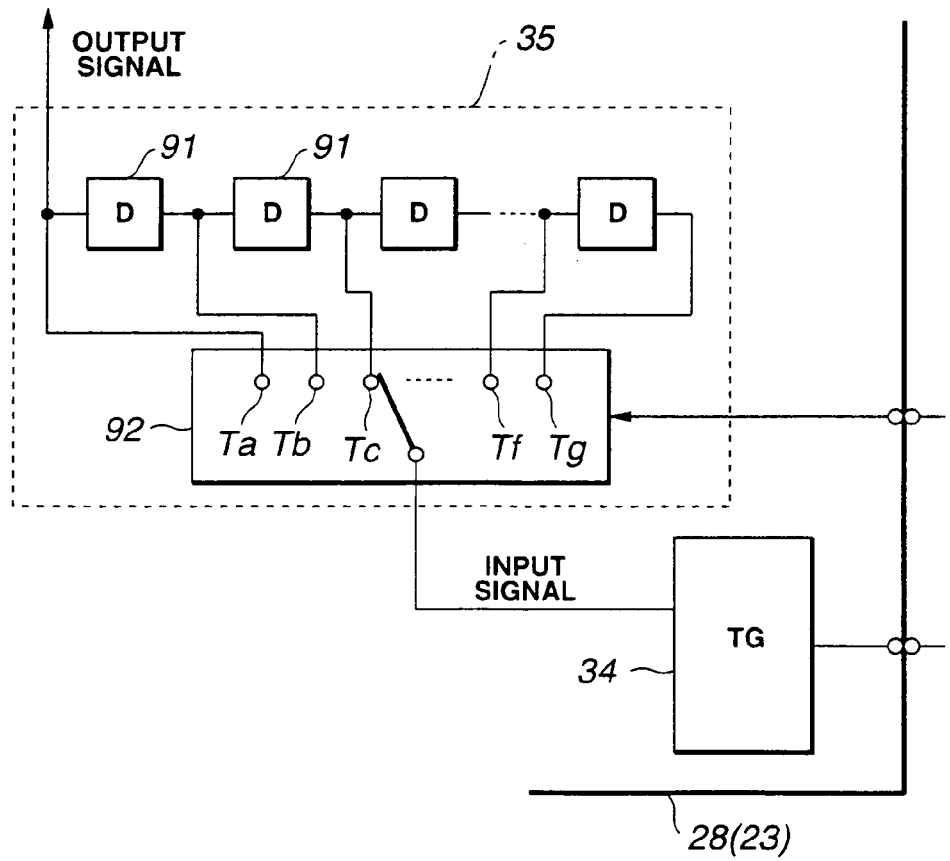

The phase adjustment circuit 35 may be formed using, for example, a plurality of delay elements 91 as shown in FIG. 11.

The phase adjustment circuit 35 consists of the delay elements 91 connected in tandem and a multiplexer 92. The delay elements 91 each produce a magnitude of delay D. The multiplexer 92 has any of terminals Ta, Tb, Tc, etc., Tf, and Tg thereof, which are connected to the delay elements 91 connected in tandem, selected. An input signal is delayed by magnitudes of delay (an integral multiple of D) produced by delay elements 91 ending with a delay element 91 connected to a selected terminal Ti of the multiplexer 92. The input signal has thus the phase thereof adjusted, whereby an output signal is provided.

A selection signal generation circuit incorporated in the CCU 6 connected to, for example, the connector 23 generates a selection signal according to which any of the terminals Ti of the multiplexer 92 is selected. The selection signal generation circuit may be formed with, for example, a DIP switch.

Figure 12:
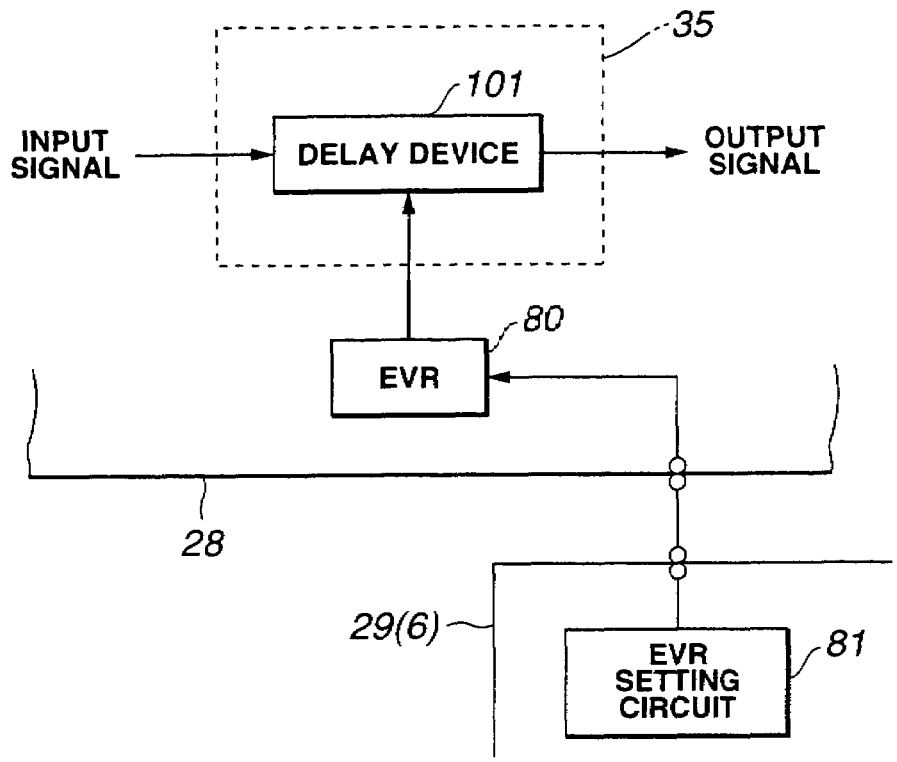
Figure 13:
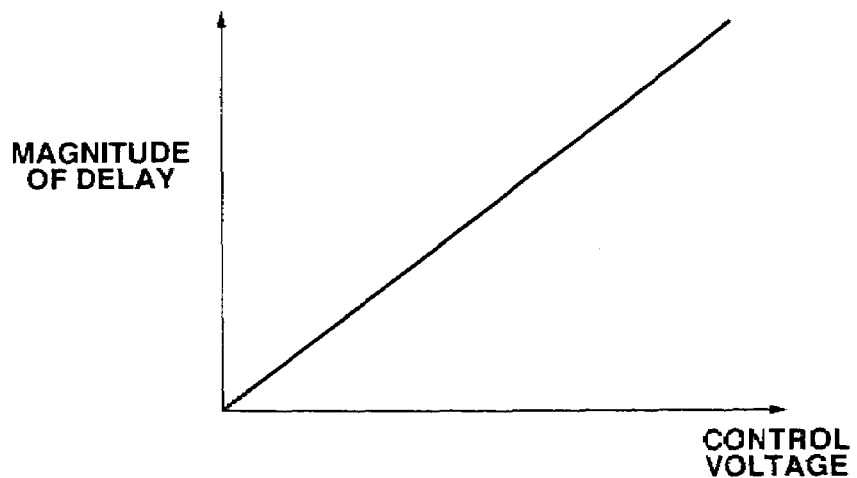

The phase adjustment circuit 35 may be formed using, as shown in FIG. 12, a delay device 101. The delay device 101 is characterized in that a magnitude of delay by which an input signal is delayed varies depending on a control voltage. The control voltage is output from the EVR 80. Thus, the phase of the input signal is adjusted.

Figure 8:
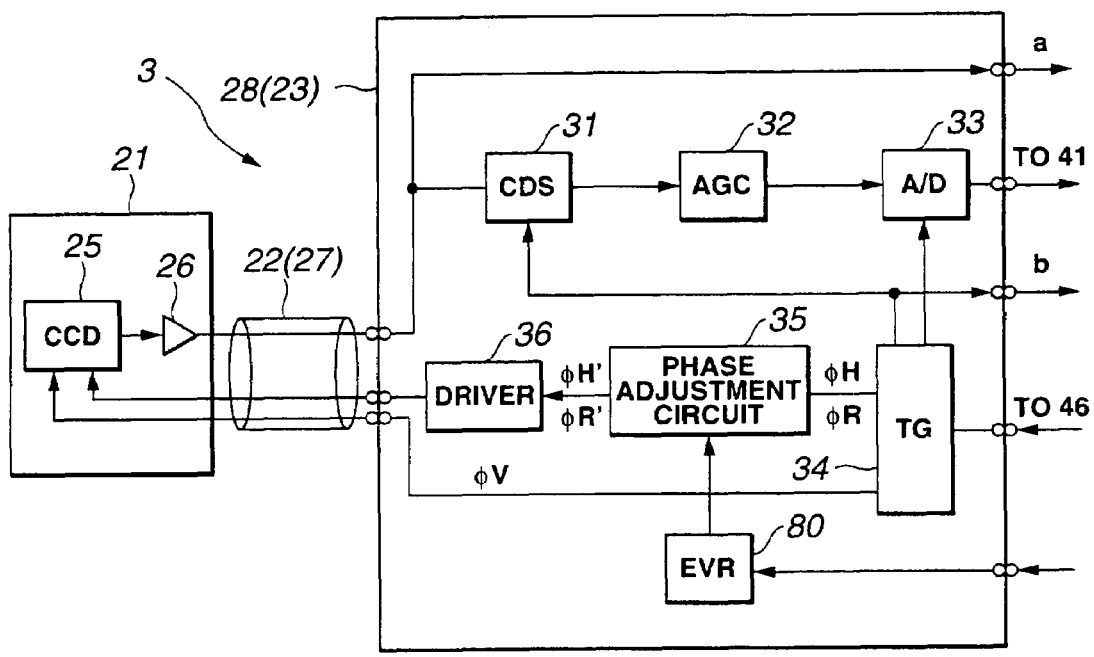
FIG. 8 to FIG. 13 relate to the second embodiment of the present invention.

Similarly to the EVR shown in FIG. 8 and FIG. 9, the EVR 80 included in the pre-processing circuit 28 is connected to the EVR setting circuit 81 included in the video processing circuit 28. The EVR setting circuit 81 is used to set a control voltage to be output from the EVR 80.

This variant exerts the same operations and advantages as the second embodiment.

Third Embodiment

Next, the third embodiment of the present invention will be described with reference to FIG. 14 to FIG. 18. The present embodiment is constructed by modifying and improving the first embodiment.

Figure 14:
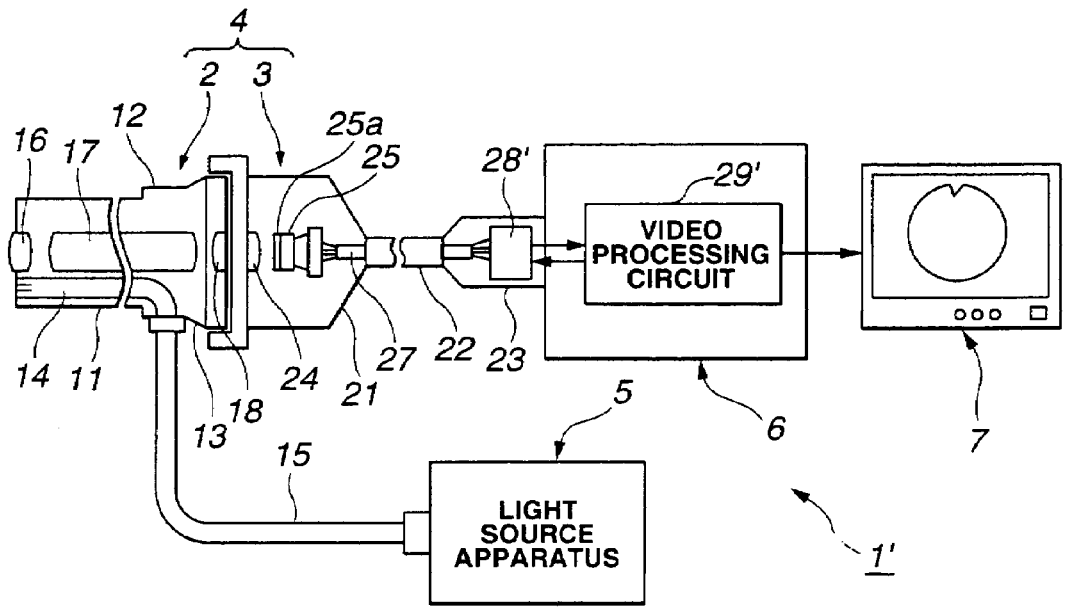
FIG. 14 to FIG. 18 relate to the third embodiment of the present invention.

An endoscopic imaging system 1' shown in FIG. 14 is different from the endoscopic imaging system 1 shown in FIG. 1 in the points described below. Namely, a processing circuit (driving adjustment circuit) 28' whose configuration is partly different from that of the pre-processing circuit 28 incorporated in the connector 23 is substituted for the pre-processing circuit 28. A video processing circuit 29' whose configuration is partly different from that of the video processing circuit 29 incorporated in the CCU 6 shown in FIG. 1 is substituted for the video processing circuit 29. These components different from the counterparts employed in the first embodiment will be specifically described below.

Figure 15:
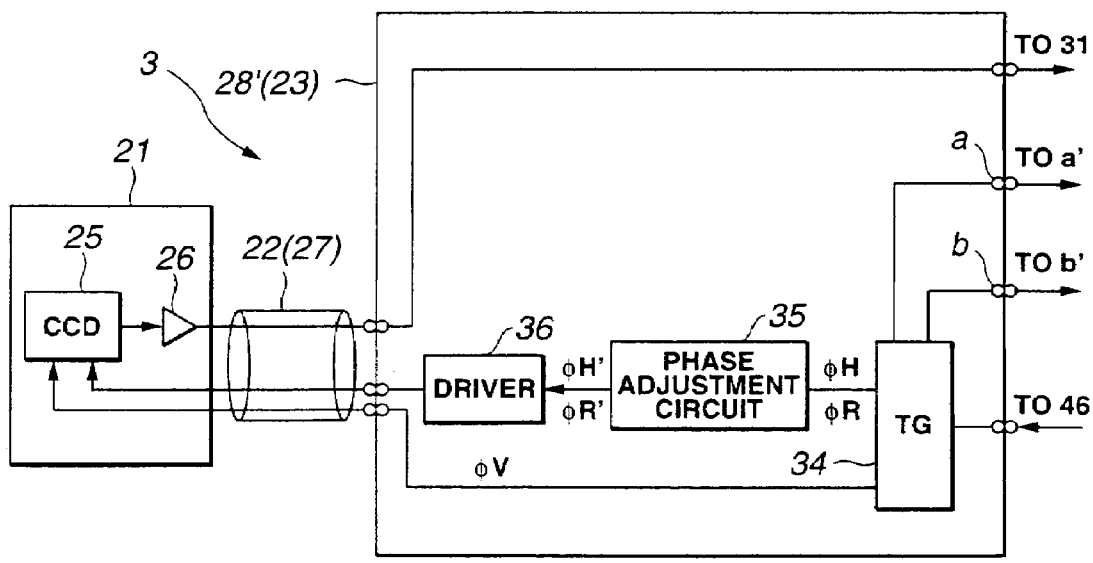

FIG. 15 shows the electric configuration of the TV camera 3. The electric configuration is partly different from that shown in FIG. 2 in the configuration of the processing circuit 28'. Specifically, the CDS circuit 31, AGC circuit 32, and A/D conversion circuit 33 included in the pre-processing circuit 28 shown in FIG. 2 are excluded. On the other hand, the video processing circuit 29' has, as shown in FIG. 16, in addition to the components of the video processing circuit 29, the CDS 31, AGC circuit 32, and A/D conversion circuit 33.

The processing circuit 28' shown in FIG. 15 has the timing generator 34, phase adjustment circuit 35, and driver 36. The configuration of the phase adjustment circuit 35 is identical to, for example, the one shown in FIG. 4.

A CCD output signal of the CCD 25 (output via the buffer 26) included in the camera head 21 is passed through the processing circuit 28' and input to the CDS circuit 31 in the video processing circuit 29'. The timing generator 34 generates CCD driving signals, applies sampling pulses to the CDS circuit 31 through (input) terminals a' and b' of the video processing circuit 29', and applies an A/D conversion clock to the A/D conversion circuit 32.

Figure 16:
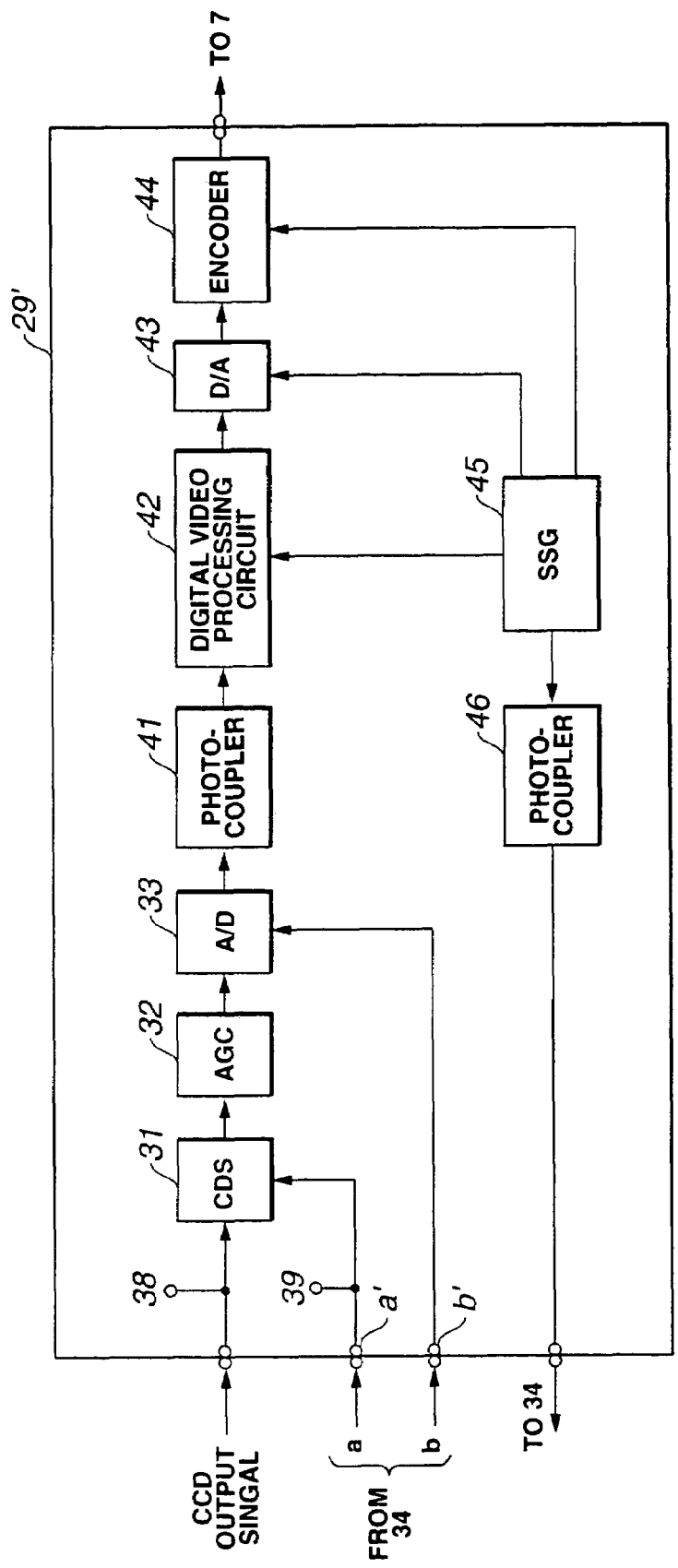

As mentioned above, the video processing circuit 29' shown in FIG. 16 is configured as if the CDS circuit 31, AGC circuit 32, and A/D conversion circuit 33 were moved from the pre-processing circuit 28 employed in the first embodiment to the video processing circuit employed therein.

To be more specific, the video processing circuit 29' employed in the present embodiment consists of the CDS circuit 31, AGC circuit 32, A/D conversion circuit 33, photocoupler 41, digital video processing circuit 42, D/A conversion circuit 43, encoder 44, sync signal generator (SSG) 45, and photocoupler 46.

A CCD output signal having passed through the processing circuit 28' is input to the CDS circuit 31. Moreover, sampling pulses are applied from the timing generator 34 to the CDS circuit 31. The timing generator 34 applies an A/D conversion clock to the A/D conversion circuit 32.

The test pins 38 and 39 are formed at an input terminal of the CDS circuit 31 and a sampling pulse input terminal of the video processing circuit. The waveforms of voltages detected at the test pins 38 and 39 are observed in order to properly adjust the phases of driving signals using the phase adjustment circuit 35.

The other components are identical to those of the first embodiment.

In the first embodiment, the A/D conversion circuit 33 is included in the pre-processing circuit 28. Digitized signals are output to the video processing circuit 29. For this reason, the number of signal lines over which the digital signals are transmitted is large. The number of pins included in the connector coupled to the video processing circuit 29 must therefore be large. According to the present embodiment, since the A/D conversion circuit 33 is included in the video processing circuit 29', the number of signal lines may be small and the connector may be of a compact type having a small number of pins.

Since the CDS circuit 31, AGC circuit 32, and A/D conversion circuit 33 are included in the common video processing circuit 29', the TV camera 3 need not have the CDS circuit 31, AGC circuit 32, and A/D conversion circuit 33. This leads to reduced costs.

The other operations and advantages are identical to those of the first embodiment.

Figure 17:
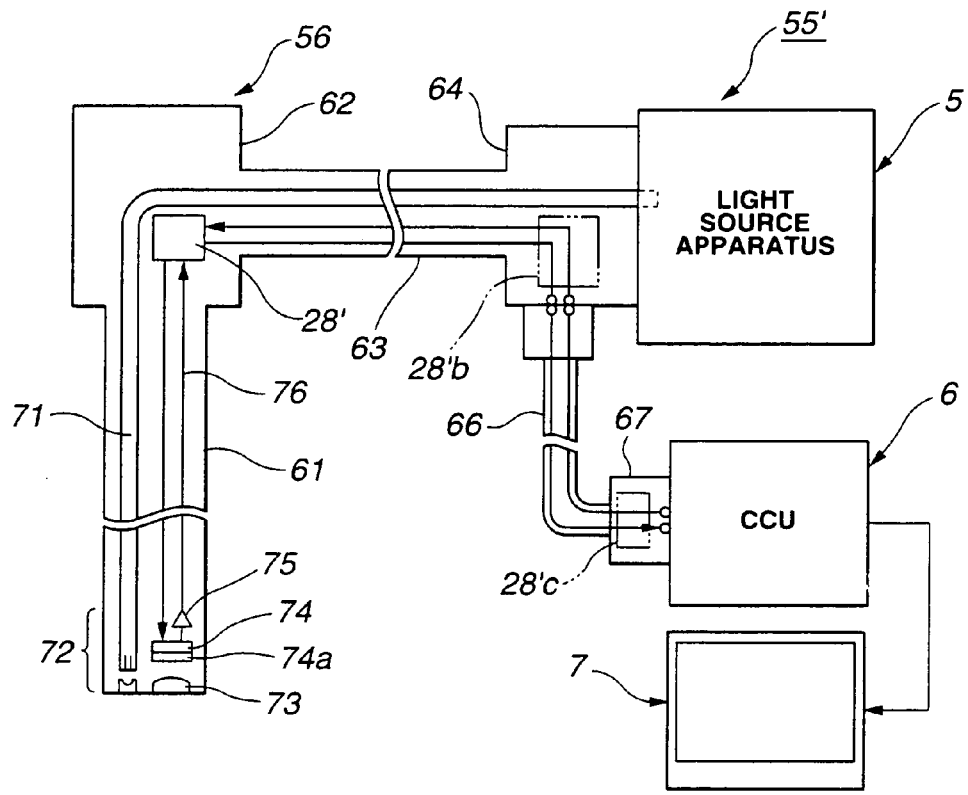

The present embodiment may be implemented in an endoscopic imaging system 55' adopting an electronic endoscope. The endoscopic imaging system 55' shown in FIG. 17 is different from the endoscopic imaging system 55 shown in FIG. 6 in the points described below. Namely, the processing circuit 28' shown in FIG. 15 is substituted for the pre-processing circuit 28, and the video processing circuit 29' shown in FIG. 16 is adopted for the CCU 6.

Referring to FIG. 17, the processing circuit 28' is incorporated in an operation unit 62 of an electronic endoscope 56. Alternatively, the processing circuit 28' may be located any position other than a position in the operation unit 62. For example, the processing circuit 28' may be located at a position 28b in a connector unit 64 or a position 28c in a connector 67 which is indicated by a double dashed line.

This variant can exert nearly the same operations and advantages as the third embodiment.

As described with reference to FIG. 6, an endoscope system may be constructed using the endoscope 4 with an external TV camera shown in FIG. 14, the electronic endoscope 56 shown in FIG. 17, and the CCU 6 for producing a video signal according to a common procedure. The endoscopes 4 and 56 are selectively removably connected to the CCU 6 so that they can be disconnected freely.

Figure 18:
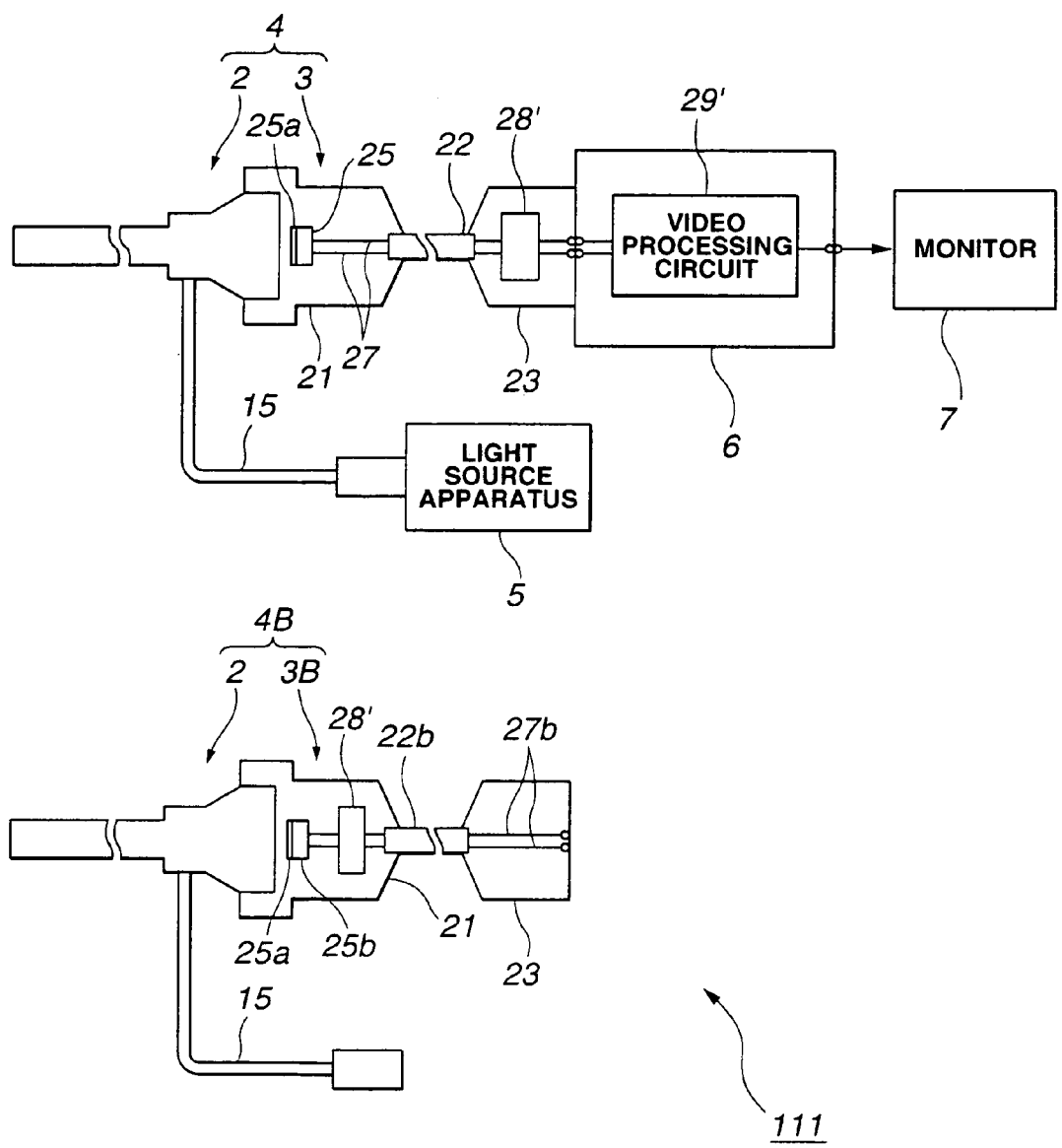

As shown in FIG. 18, an endoscope system 111 may be constructed using endoscopes with an external TV camera 4 and 4B that have camera cables 22 and 22b extended therefrom. The camera cables 22 and 22b contain different signal cables 27 and 27b.

The endoscope system 111 consists of the endoscopic imaging system 1' shown in FIG. 14 and the second endoscope 4B with an external TV camera.

The second endoscope 4B with an external TV camera consists mainly of the optical endoscope 2 and a TV camera 3B to be mounted on the optical endoscope 2 so that it can be dismounted freely.

The TV camera 3B consists mainly of a camera head 21 having a CCD 25b incorporated therein, a camera cable 22b, and a connector 23 attached to the end of the camera cable 22b. The first TV camera 3 has the processing circuit 28' incorporated in the connector 23 thereof, while the second TV camera 3B has the processing circuit 28' incorporated in the camera head 21 thereof.

The CCD 25b offers a different number of pixels from the CCD 25. The other components are identical to those described previously.

Even in the case of the endoscope system 111, the endoscopes offering different numbers of pixels and having signal cables of different lengths extended therefrom can be coped with using the CCU 6 in common.

As shown in FIG. 18, there is the merit that the processing circuit 28' (or the pre-processing circuit 28) can be located at any position on the signal cable 27 (or 27b) linking the CCD 25 and CCU 6. Incidentally, in the electronic endoscope shown in FIG. 17, the processing circuit 28' may be located at, aside from the illustrated position, any position within the distal part 72.

Fourth Embodiment

Next, the fourth embodiment of the present invention will be described with reference to FIG. 19 and FIG. 20. The configuration of the present embodiment is slightly different from that of the third embodiment.

An endoscopic imaging system of the present embodiment has a processing circuit 28" and a video processing circuit 29" whose configurations are slightly different from those of the processing circuit 28' and video processing circuit 29' employed in the endoscopic imaging system 1' shown in FIG. 14.

To be more specific, according to the third embodiment, the phases of driving signals are adjusted manually. According to the present embodiment, an electronic voltage regulator controllable by a setting circuit is adopted.

Figure 19:
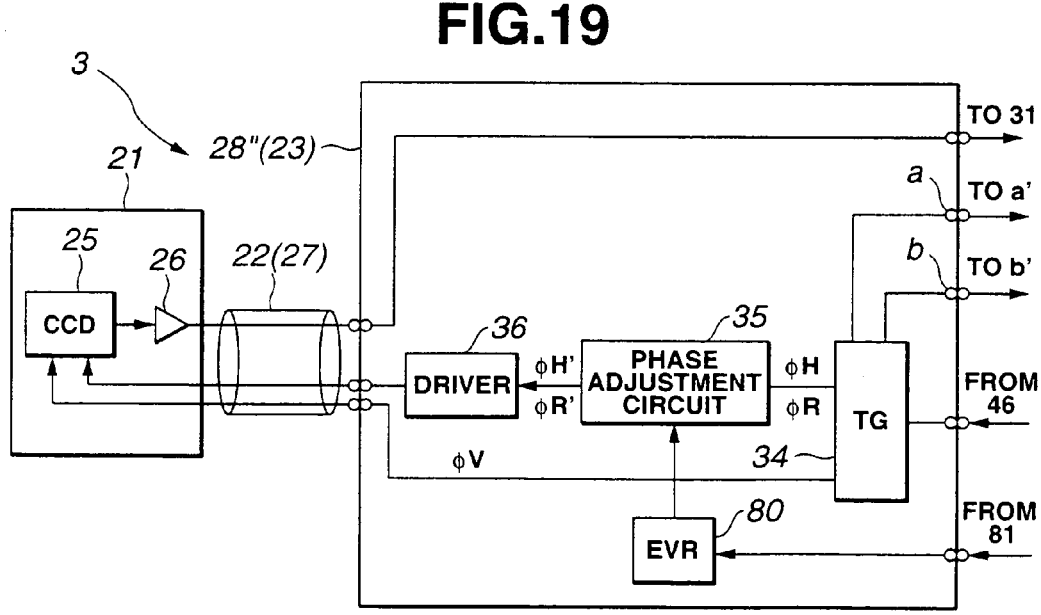

As seen from the electric configuration of the TV camera 3 shown in FIG. 19, the processing circuit 28" has, in addition to the same components as those of the processing circuit 28, shown in FIG. 15, the electronic voltage regulator (abbreviated to an EVR) 80. The EVR 80 assists the phase adjustment circuit 35 in adjusting the phases of driving signals.

The EVR 80 is electrically connected to the EVR setting circuit 81 included in the video processing circuit 28" shown in FIG. 20. With a control signal output from the EVR setting circuit 81 in the CCU 6, a voltage output from the EVR 80 can be controlled.

In other words, the video processing circuit 28" shown in FIG. 20 has, in addition to the same components as those of the video processing circuit 28' shown in FIG. 16, the EVR setting circuit 81.

The phase adjustment circuit 35 operates in cooperation with the EVR 80 in the same manner as that shown in FIG. 10 or FIG. 12. The description will therefore be omitted.

The plurality of delay elements 91 shown in FIG. 11 may be used to form the phase adjustment circuit 35.

The present embodiment has the same advantages as the third embodiment. In addition, since the phases of driving signals are adjusted via the EVR 80 using the CCU 6, a regulating means such as a trimmer or a variable resistor need not be included in the connector 23. Moreover, a regulation hole used for regulation need not be bored in the connector unit. A design for fully sealing the connector 23 can therefore be adopted, and the TV camera 3 can be readily structured to be waterproof. Besides, the efficiency in shielding components from electromagnetic waves can be improved.

Finally, embodiments formed as combinations of parts of the aforesaid embodiments will belong to the present invention.

What is claimed is:

1. An endoscopic imaging system comprising:
an endoscope having an insertion unit which is insertable into an object, the insertion unit having an illumination optical system for illuminating the object and an objective optical system for forming an optical image of the illuminated object;
an imaging apparatus having an imaging device for picking up the optical image and outputting an image pick-up signal;
a camera control unit connected to the imaging apparatus, the camera control unit comprising a synchronizing signal generation circuit for generating a synchronizing signal, and a video signal processing circuit for processing the image pick-up signal at a predetermine timing based on the synchronizing signal, to generate a video signal; and
a connector for connecting the imaging apparatus and the camera control unit, the connector being provided to the imaging apparatus and electrically connected to the imaging device via an elongate signal transmission line, the connector including:
a timing signal generation circuit for generating a periodic timing signal according to the type of the imaging device;
a sampling circuit for sampling the image pick-up signal at a predetermined sampling timing according to the timing signal, and outputting the sampled image pick-up signal to the video signal processing circuit;
a phase delay circuit for delaying the phase of the timing signal by a delay amount according to the length of the signal transmission line; and
an imaging device drive circuit for generating a drive signal to drive the imaging device and inputting the generated drive signal to the imaging device based on the timing signal, the phase of which has been delayed by the phase delay circuit.

2. An endoscopic imaging system according to claim 1, wherein the phase adjustment circuit adjusts the phases of the timing signals so that an output signal of the imaging device to be input to the video processing unit will be in phase with a predetermined timing signal produced in the video processing unit.

3. An endoscopic imaging system according to claim 2, wherein the phase adjustment circuit adjusts the phases of the timing signals according to a sampling timing of the sampling circuit.

4. An endoscopic imaging system according to claim 3, wherein at least one of the imaging apparatus and the video processing unit further has an analog-to-digital conversion circuit for digitizing an analog output signal of the imaging apparatus according to a timing signal generated by the timing signal generation circuit.

5. An endoscopic imaging system according to claim 3, wherein at least one of the imaging apparatus and the video processing unit further has checking terminals used to check phase differences between the timing signals generated by the timing signal generation circuit and an output signal of the imaging device having passed through the signal transmission line.

6. An endoscopic imaging system according to claim 3, wherein the phase adjustment circuit adjusts the phases of the timing signals by adjusting a resistance of a variable resistor.

7. An endoscopic imaging system according to claim 3, wherein the phase adjustment circuit adjusts the phases of the timing signals by adjusting an output voltage of an electronic voltage regulator.

8. An endoscopic imaging system according to claim 7, wherein the video processing unit has an electronic voltage regulator voltage setter for setting an output voltage of the electronic voltage regulator.

9. An endoscopic imaging system according to claim 3, wherein the phase adjustment circuit adjusts the phases of the timing signals by selecting one of a plurality of delay elements connected in tandem.

10. An endoscopic imaging system according to claim 3, wherein the phase adjustment circuit adjusts the phases of the timing signals by employing a delay device for producing a delay, of which the magnitude is varied depending on an applied voltage.

11. An endoscopic imaging system according to claim 3, wherein the endoscope is an optical endoscope having a propagation optical system for propagating the optical image, and the imaging apparatus is a TV camera mounted on the optical endoscope and having the imaging device, which picks up the optical image propagated by the propagation optical system, incorporated therein.

12. An endoscopic imaging system according to claim 3, wherein the endoscope is an electronic endoscope having the imaging device located at the position of the image plane of the objective optical system, and the electronic endoscope has the imaging apparatus incorporated therein.

13. An endoscopic imaging system according to claim 3, wherein the phase adjustment circuit adjusts the phases of the timing signals, that is, a horizontal driving signal used to horizontally drive the imaging device and a reset signal used to reset the imaging device according to the sampling timing.

14. An endoscopic imaging system comprising:
an optical endoscope having an insertion unit which is insertable into an object, the insertion unit having an illumination optical system for illuminating the object, an objective optical system for forming an optical image of the illuminated object, and a propagation optical system for propagating the optical image;
an imaging apparatus mounted on the optical endoscope and having an imaging device for picking up the optical image of the object propagated by the propagation optical system and outputting an image pick-up signal;
a camera control unit connected to the imaging apparatus, the camera control unit comprising a synchronizing signal generation circuit for generating a synchronizing signal, and a video signal processing circuit for processing the image pick-up signal at a predetermine timing based on the synchronizing signal, to generate a video signal; and
a connector for connecting the imaging apparatus and the camera control unit, the connector being provided to the imaging apparatus and electrically connected to the imaging device via an elongate signal transmission line, the connector including:
a timing signal generation circuit for generating a periodic timing signal according to the type of the imaging device;
a sampling circuit for sampling the image pick-up signal at a predetermined sampling timing according to the timing signal, and outputting the sampled image pick-up signal to the video signal processing circuit;
a phase delay circuit for delaying the phase of the timing signal by a delay amount according to the length of the signal transmission line; and
an imaging device drive circuit for generating a drive signal to drive the imaging device and inputting the generated drive signal to the imaging device based on the timing signal, the phase of which has been delayed by the phase delay circuit.

15. An endoscopic imaging system according to claim 14, wherein the connector unit has the timing signal generation circuit and the phase adjustment circuit.

16. An endoscopic imaging system according to claim 14, wherein the camera head has the timing signal generation circuit and the phase adjustment circuit.

17. An endoscopic imaging system comprising:
an electronic endoscope having an insertion unit which is insertable into an object, the insertion unit having an illumination optical system for illuminating the object, an objective optical system for introducing an optical image of the illuminated object, and an imaging device located at the position of the image plane of the objective optical system for picking up the optical image and outputting an image pick-up signal;
a camera control unit connected to the electronic endoscope, the camera control unit comprising a synchronizing signal generation circuit for generating a synchronizing signal, and a video signal processing circuit for processing the image pick-up signal at a predetermine timing based on the synchronizing signal, to generate a video signal; and
a connector for connecting the electronic endoscope and the camera control unit, the connector being provided to the electronic endoscope and electrically connected to the imaging device via an elongate signal transmission line, the connector including:
a timing signal generation circuit for generating a periodic timing signal according to the type of the imaging device based on the synchronizing signal;
a sampling circuit for sampling the image pick-up signal at a predetermined sampling timing according to the timing signal, and outputting the sampled image pick-up signal to the video signal processing circuit;
a phase delay circuit for delaying the phase of the timing signal by a delay amount according to the length of the signal transmission line; and an imaging device drive circuit for generating a drive signal to drive the imaging device and inputting the generated drive signal to the imaging device based on the timing signal, the phase of which has been delayed by the phase delay circuit.

18. An image apparatus comprising:

an imaging device having an imaging device for picking up an image of an object and generating an image pick-up signal; and a connector electrically connected to the imaging device via an elongate signal transmission line, the connector including:

- a timing signal generation circuit for generating a periodic timing signal according to the type of the imaging device;
- a sampling circuit for sampling the image pick-up signal at a predetermined sampling timing according to the timing signal;
- a phase delay circuit for delaying the phase of the timing signal by a delay amount according to the length of the signal transmission line; and
- an imaging device drive circuit for generating a drive signal to drive the imaging device and inputting the generated drive signal to the imaging device based on the timing signal, the phase of which has been delayed by the phase delay circuit;

wherein the sampling circuit performs the sampling at a timing of a constant phase relation with respect to the image pick-up signal even when the length of the signal transmission line is different.

19. The image apparatus according to claim 18, wherein the imaging device is provided with an endoscope camera head connected to an optical endoscope and picks up an optical image to be displayed by the optical endoscope.

20. The image apparatus according to claim 18, wherein the imaging apparatus is an electronic endoscope having an insertion unit which is insertable into a body cavity, the imaging device being provided at a distal end of the insertion unit.

21. The image apparatus according to claim 18, wherein the sampling circuit samples feedthrough and a signal wave of the image pick-up signal at a timing of a constant phase relation where the feedthrough and the signal wave of the image pick-up signal are inputted.

* * * * *